(12) United States Patent
Lichtenhan et al.

(10) Patent No.: US 6,911,518 B2
(45) Date of Patent: Jun. 28, 2005

(54) POLYHEDRAL OLIGOMERIC -SILSESQUIOXANES, -SILICATES AND -SILOXANES BEARING RING-STRAINED OLEFINIC FUNCTIONALITIES

(75) Inventors: Joseph D. Lichtenhan, San Juan Capistrano, CA (US); Joseph J. Schwab, Huntington Beach, CA (US); Yi-Zong An, Fountain Valley, CA (US); William Reinerth, Westminster, CA (US); Frank J. Feher, Costa Mesa, CA (US)

(73) Assignee: Hybrid Plastics, LLC, Fountain Valley, CA (US)

( * ) Notice: Subject to any disclaimer, the term of this patent is extended or adjusted under 35 U.S.C. 154(b) by 0 days.

(21) Appl. No.: 09/747,762

(22) Filed: Dec. 21, 2000

(65) Prior Publication Data

US 2004/0068075 A1 Apr. 8, 2004

Related U.S. Application Data

(60) Provisional application No. 60/171,888, filed on Dec. 23, 1999.

(51) Int. Cl.[7] .......................... C08G 77/08; C08G 77/20
(52) U.S. Cl. .............................. 528/15; 528/15; 528/25; 528/27; 528/31; 528/33; 528/34; 528/36; 528/40; 528/42; 528/451; 528/453; 528/465; 528/478; 528/479; 528/489
(58) Field of Search .............................. 528/15, 25, 27, 528/31, 33, 34, 36, 40, 42; 556/451, 453, 465, 478, 479, 489

(56) References Cited

U.S. PATENT DOCUMENTS

| | | | |
|---|---|---|---|
| 3,390,168 A | 6/1968 | Brown | 260/448.2 |
| 4,381,396 A | 4/1983 | Ryang | 549/237 |
| 4,657,965 A | 4/1987 | Watanabe et al. | 524/506 |
| 4,900,779 A | 2/1990 | Leibfried | 524/862 |
| 5,008,360 A | 4/1991 | Bard et al. | 528/25 |
| 5,034,490 A | 7/1991 | Jacobine et al. | 528/30 |
| 5,190,808 A | 3/1993 | Tenney et al. | 428/224 |
| 5,194,489 A | 3/1993 | Frances et al. | 524/731 |
| 5,412,053 A | 5/1995 | Lichtenhan et al. | 528/9 |
| 5,484,867 A | 1/1996 | Lichtenhan et al. | 528/9 |
| 5,589,562 A | 12/1996 | Lichtenhan et al. | 528/9 |
| 5,939,576 A | 8/1999 | Lichtenhan et al. | 556/460 |
| 5,942,638 A | 8/1999 | Lichtenhan et al. | 556/460 |
| 6,075,068 A | 6/2000 | Bissinger | 523/116 |

OTHER PUBLICATIONS

Haddad, T.S. et al. Hybrid, Norbornenyl–Based Polyhedral Oligosilsesquioxane (POSS) Polymers. J. Am. Chem. Soc. Polym. Preprints. Jan. 1997. vol. 38, No. 1. pp. 127–128.

Mather, P.T. et al. Mechanical Relaxation and Microstructure of Poly (norbornyl–POSS) Copolymers. Macromolecules. Feb. 1999. vol. 32. pp. 1194–1203.

*Primary Examiner*—Jeffrey B. Robertson
(74) *Attorney, Agent, or Firm*—David Jaffer; Pillsbury Winthrop LLP

(57) ABSTRACT

Processes have been developed for the manufacture of polyhedral oligomeric silsesquioxanes (POSS), polysilsesquioxanes, polyhedral oligomeric silicates (POS), and siloxane molecules bearing reactive ring-strained cyclic olefins (e.g. norbornenyl, cyclopentenyl, etc. functionalities). The preferred manufacturing processes employ the silation of siloxides (Si—OA, where A=H, alkaline or alkaline earth metals) with silane reagents that contain at least one reactive ring-strained cyclic olefin functionality [e.g., $X_{3-y}Si(CH_3)_y(CH_2)_2$ where y=1–2 and X=OH, Cl, Br, I, alkoxide OR, acetate OOCR, peroxide OOR, amine $NR_2$, isocyanate NCO, and R]. Alternatively, similar products can be prepared through hydrosilation reactions between silanes containing at least one silicon-hydrogen bond (Si—H) with ring-strained cyclic olefin reagents [e.g., 5-vinyl, 2 norbornene $CH_2$=CH, cyclopentadiene]. The two processes can be effectively practiced using polymeric silsesquioxanes $[RSiO_{1.5}]_\infty$ where $\infty$=1–1,000,000 or higher and which contain unreacted silanol or silane groups at chain terminus or branch points, on POSS nanostructures of formulas $[(RSiO_{1.5})_n]_{\Sigma\#}$, homoleptic, $[(RSiO_{1.5})_m(R'SiO_{1.5})_n]_{\Sigma\#}$, heteroleptic, and $\{(RSiO_{1.5})_m(RXSiO_{1.0})_n\}_{\Sigma\#}$, functionalized heteroleptic nanostructures, on silanes $RSiX_3$, linear, cyclic, oligomeric and polymeric siloxanes (polymeric formula $RX_2Si$—$(OSiRX)_m$—$OSiRX_2$ where m=0–1000, X=OH, Cl, Br, I, alkoxide OR, acetate OOCR, peroxide OOR, amine $NR_2$, isocyanate NCO, and R). Each of the processes result in new chemical species bearing one or more ring strained olefins that can undergo polymerization, grafting, or other desirable chemical reactions to form polymeric products. These polymeric systems are most desirably utilized in polymerizations for the modification of properties of thermoplastic or thermoset resin systems or for the preparation of polymers with utility in electronics, medical devices, sporting goods, and aerospace as coatings and structural components.

7 Claims, 3 Drawing Sheets

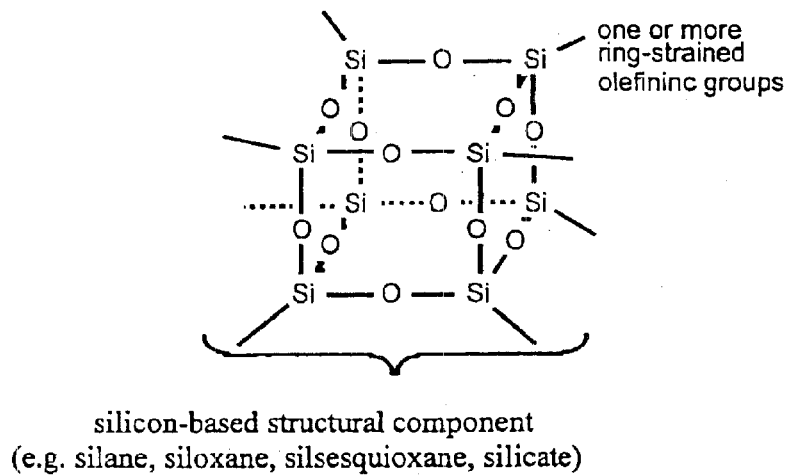
silicon-based structural component
(e.g. silane, siloxane, silsesquioxane, silicate)
Figure 1. Generic anatomy of invention
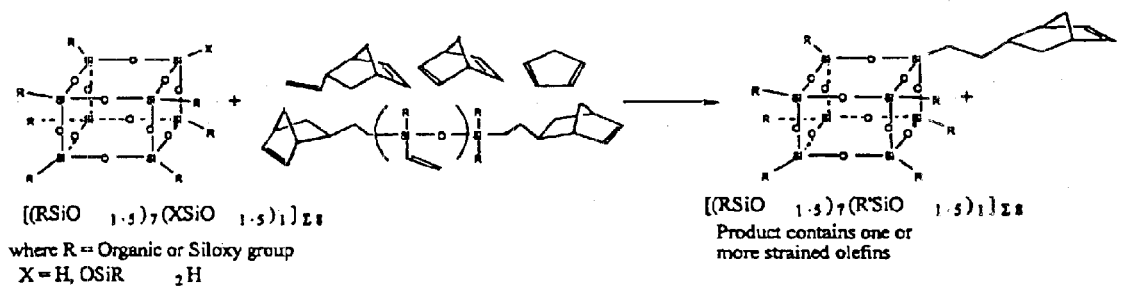
Figure 2: Hydrosilation method for attaching ROMP group. Only monohydrosilation is shown, polyhydrosilations can also be carried out.

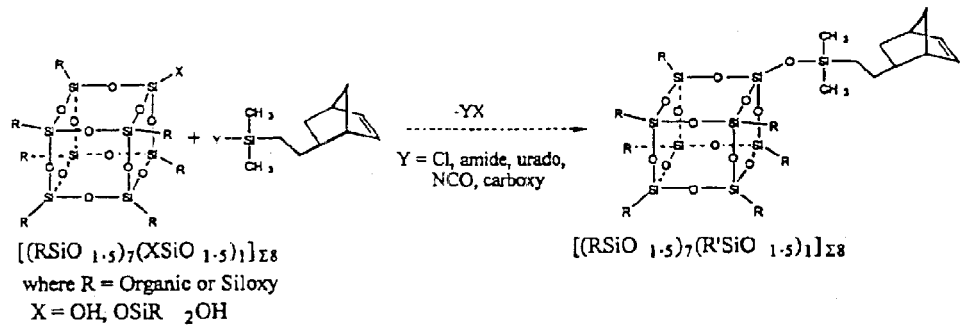
Figure 3. Silation method for attaching ROMP group. Monosilation was shown, polysilations can also be carried out.
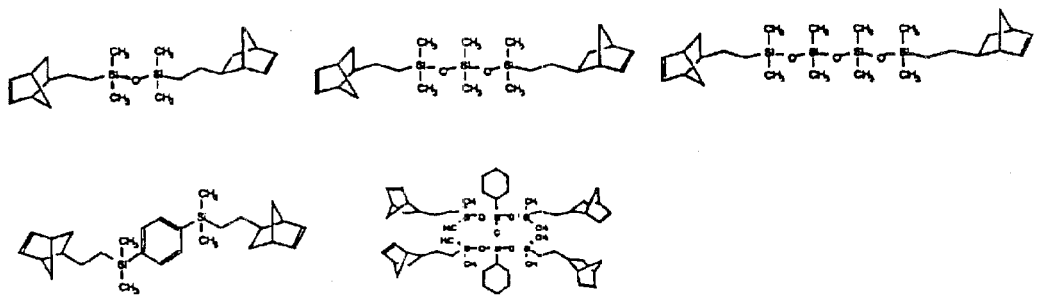
Fiture 4. Representative examples of non-nanostructured oligomeric siloxane and silsesquioxane systems.

POLYHEDRAL OLIGOMERIC -SILSESQUIOXANES, -SILICATES AND -SILOXANES BEARING RING-STRAINED OLEFINIC FUNCTIONALITIES

This application claims the benefit of Provisional Application No. 60/171,888, filed Dec. 23, 1999.

BACKGROUND OF THE INVENTION

1. Field of the Invention

The present invention relates generally to methods of preparing hybrid "organic-inorganic" chemical compositions that are wholly useful by themselves or in combination with other comonomers for producing novel polymeric compositions with desirable physical properties such as adhesion to polymeric, composite and metal surfaces, water repellency, low dielectric constant, resistance to abrasion and fire, biological compatibility, and optical quality plastics. The new compositions reported herein contain two primary material combinations.

Part one of the combination is a silicon component which may be comprised of a silane, silicone, silsesquioxane, polyhedral oligomeric silsesquioxane, silicate, polyhedral oligomeric silicate or combinations thereof. The silicon-component provides chemical oxidation resistance, thermal stability, and structural reinforcement to the overall molecule. The second component of the composition is one or more ring strained olefinic groups. The ring strained olefinic groups provide the primary reactive functionality for polymerization and for solubilization. The ring strained olefin may be comprised in whole or part from primarily olefinic carbon-based rings (e.g. cyclo-propyl, butenyl, pentenyl, hexenyl, norbornenyl). In some cases one or more hetero atoms such as N, O, S, P, B may also be included in the strained olefinic ring (e.g. ring strained cyclic olefinic imides or ethers).

2. Brief Description of the Prior Art

Prior art has demonstrated that strained olefinic rings can be utilized in polymerizations using free radical and UV initiators and transition metal based catalysts. See Haddad et al., J. Amer. Chem. Soc. Polym. Preprints Vol 38, No 1. 1997, pp 127–128, and Mather et. al. Macromolecules Vol 32, (1999), pp 1194–1203 (utility of POSS-polynorbornenes); G. Odian, Principles of Polymerization, 3rd Ed. John Wiley & Sons, (1991) p 578 (polynorbornenes and their utility). Prior art by Tenney et al in U.S. Pat. No. 5,190,808 described the use of silane-substituted monomers containing only one strained ring olefin, per silicon, for the preparation of prepregs for the construction of printed circuit boards. This art was limited in scope and conception and did not fulfill the need for the development of other silicon based strained ring olefin systems that could serve as crosslinkers and zero volatile organic comonomers or as resin systems for use in the manufacture of electronic, medical, sporting goods, aerospace and automotive components, packaging and personal care products. Prior art by Leibfried in U.S. Pat. No. 4,900,779 reported the process of using the hydrosilation of hydridosilanes and strained ring olefins for the purposes of forming crosslinked network materials having tailorable physical properties. Leibfried does not teach methods that allow for the preparation and isolation of silicone, silane, polyhedral oligomeric silsesquioxane or polyhedral oligomeric silicates that bear olefinic strained rings. Nor did they teach the use of such isolable intermediate species for subsequent utility in ROMP polymerizations. Leibfried was also silent as to the usage of silation as method of preparing such materials rather only a hydrosilation method was taught for the attachment of the strained olefinic group to the silane silicon atoms. Literature by Hambley et al. report the preparation of silsesquioxane materials bearing a norbornyl functionality for the purposes of steric bulk and solubility. They did not utilize a strained ring olefinic type of norbornene group and they did not teach the use of such a derivative for polymerization purposes. See Hambley, et al., Applied Organometallic Chemistry (1992) Vol 6 No. 3, pp 253–260.

SUMMARY OF THE INVENTION

It is an objective of this invention to teach the preparation of silicon-based monomers, oligomers, polymers and nanostructures that bear one and more strained ring olefinic functionalities per molecule. When such compositions exist as solids, waxes or oily liquids, they are particularly desirable as low and zero volatility monomers and resins. The viscosity and melting point of such systems can be controlled through the molecular weight, composition and tertiary structure of the molecules. Solid versions of these molecules can exist with crystalline or amorphous solid-state structures. Both forms (solid and liquid) can be utilized as nanoreinforcements and as fillers in thermoplastics and thermoset systems, while all systems bearing more than one strained ring olefin can be used as high temperature crosslinkers and curatives in rubber, silicones, imides, and other olefin based polymers. It is desirable to incorporate strained ring olefins onto silicone, silsesquioxane, polyhedral oligomeric silsesquioxane, silicate and polyhedral oligomeric silicate for the purposes of improving biocompatability, hardness, fire resistance, oxidation resistance, and mechanical durability.

This invention teaches two processes that enable the preparation of strained olefin bearing silanes, siloxanes, silsesquioxanes, polyhedral oligomeric silsesquioxane, silicates and polyhedral oligomeric silicate from readily available feedstocks. The preferred manufacturing processes employ the silation of siloxides (Si—OA, where A=H, alkaline or alkaline earth metals) with silane reagents bearing at least one reactive ring-strained cyclic olefin functionality [e.g.,

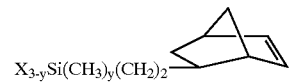

$X_{3-y}Si(CH_3)_y(CH_2)_2$— where y=1–2 and X=OH, Cl, Br, I, alkoxide OR, acetate OOCR, peroxide OOR, amine $NR_2$, isocyanate NCO, and R]. Alternatively, the same or closely related products can be prepared through the hydrosilation reaction between silanes bearing at least one silicon-hydrogen bond (Si—H) with ring-strained cyclic olefin reagents [e.g., 5-vinyl, 2 norbornene

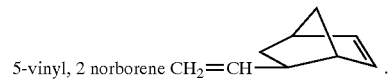

5-vinyl, 2 norborene $CH_2=CH$—

The processes can be effectively practiced using polymeric silsesquioxanes $[RSiO_{1.5}]_\infty$ where $\infty=1–1,000,000$ or higher and which contain unreacted silanol or silane groups at chain terminus or branch points, on POSS nanostructures of formulas $[(RSiO_{1.5})_n]_{\Sigma\#}$, homoleptic, $[(RXSiO_{1.5})_n]_{\Sigma\#}$, functionalized homoleptic, $[(RSiO_{1.5})_m(R'SiO_{1.5})_n]_{\Sigma\#}$, heteroleptic, and $[(RSiO_{1.5})_m(RXSiO_{1.0})_n]_{\Sigma 3\#}$, functionalized heteroleptic nanostructures, or on silanes $RSiX_3$, or on linear, cyclic, oligomeric and polymeric siloxanes (polymeric formula $RX_2Si$—$(OSiRX)_m$—$OSiRX_2$ where m=0–1000, X=OH, Cl, Br, I, alkoxide OR, acetate OOCR, peroxide OOR, amine $NR_2$, isocyanate NCO, and R).

The advantages of the present invention will become apparent to those skilled in the art after having read the following detailed description of the preferred embodiment which is illustrated in the several figures of the drawing.

DEFINITION OF FORMULA REPRESENTATIONS FOR NANOSTRUCTURES

For the purposes of understanding this invention's chemical compositions the following definition for formula representations of Polyhedral Oligomeric Silsesquoxane (POSS) and Polyhedral Oligomeric Silicate (POS) nanostructures is made.

Polysilsesquioxanes are materials represented by the formula $[RSiO_{1.5}]_\infty$ where ∞=molar degree of polymerization and R=organic substituent (H, siloxy, cyclic or linear aliphatic or aromatic groups that may additionally contain reactive functionalities such as alcohols, esters, amines, ketones, olefins, ethers or halides). Polysilsesquioxanes may be either homoleptic or heteroleptic. Homoleptic systems contain only one type of R group while heteroleptic systems contain more than one type of R group.

POSS and POS nanostructure compositions are represented by the formula:

$[(RSiO_{1.5})_n]_{\Sigma\#}$ for homoleptic compositions $[(RSiO_{1.5})_m(R'SiO_{1.5})_n]_{\Sigma\#}$ for heteroleptic compositions (where R≠R')

$[(RSiO_{1.5})_m(RXSiO_{1.0})_n]_{\Sigma\#}$ for functionalized heteroleptic compositions (where R groups can be equivalent or inequivalent)

In all of the above R is the same as defined above and X includes but is not limited to OH, Cl, Br, I, alkoxide (OR), acetate (OOCR), peroxide (OOR), amine ($NR_2$) isocyanate (NCO), and R. The symbols m and n refer to the stoichiometry of the composition. The symbol $\Sigma$ indicates that the composition forms a nanostructure and the symbol # refers to the number of silicon atoms contained within the nanostructure. The value for # is usually the sum of m+n. It should be noted that $\Sigma\#$ is not to be confused as a multiplier for determining stoichiometry, as it merely describes the overall nanostructural characteristics of the system (aka cage size).

IN THE DRAWING

FIG. 1 illustrates the generic anatomy of the invention;

FIG. 2 shows a hydrosilation method for attaching a ROMP group (only monohydrosilation is shown; polyhydrosilations can also be carried out);

FIG. 3 shows a silation method for attaching a ROMP group (monosilation shown; polysilations can also be carried out);

FIG. 4 shows representative examples of non-nanostructured oligomeric siloxane and silsesquioxane systems;

DETAILED DESCRIPTION OF THE PREFERRED EMBODIMENT

This invention teaches the use of two different chemical processes for the preparation of hybrid (organic-inorganic) silicon-based molecular systems which contain strained organic groups. The process depicted in FIG. 2 depicts a general hydrosilation reaction of a POSS-silane with a vinyl or other olefinic group on a molecule that also contains a ring-strained olefinc group. The reaction is effectively carried out with the aid of a late-metal catalyst such as Karstedt's catalyst (at concentration ranges from 0.01 to 5 wt %) (see e.g. U.S. Pat. No. 3,814,730), Speier's catalyst (hexachloroplatinic acid in 2-propanol), and 5% palladium supported on carbon. The hydrosilation reaction effectively promotes the oxidative addition of the silicon-hydride bond from the silane across the olefinic carbon-carbon double bond of the strained-ring olefin bearing compositions claimed herein. The hydrosilation is an effective and reliable process for the addition of strained ring olefins to most silanes, carbosilanes, siloxanes, POSS, and POS systems. The hydrosilation process can produce undesirable isomeric products or impurities that consequently may necessitate purification of the final product to obtain the desired product performance level. The hydrosilation procedure is desirable because of the commercial availability of silicon-based molecules bearing hydride functionalities and vinyl and olefin bearing strained olefinc functionalities.

In cases where the hydrosilation process does not produce satisfactory product compositions or where the method cannot be applied due to the chemical nature of the starting materials, an alternate method of synthesis has been developed. The process in FIG. 3 depicts a general silation reaction of a POSS-silanol (or the anionic siloxide equivalent) with a halide (or functional equivalent) silane coupling agent that bears a strained olefinic group. The reaction is desirable because it does not require the use of a metal catalyst and the process is often less exothermic and more selective that the hydrosilation technique. The silation reaction effectively promotes the silation of the silicon atoms in each component through the formation of strong silicon-oxygen-silicon linkages in the desired final product composition. The reaction is also driven by the formation of salts or acidic byproducts that can be removed from the reaction medium using standard trapping, extraction or precipitation methods. The silation procedure is also desirable because of the commercial availability of silicon-based molecules bearing silanol, siloxide, hydroxy, alkoxy groups and silanes bearing strained olefinc functionalities.

Structural representations of specific telechelic compositions that are claimed and which can be prepared using the above procedures are shown in FIG. 4. These compositions are in no way limiting and are shown to illustrate the diversity and utility of the described processes.

Figure 5:
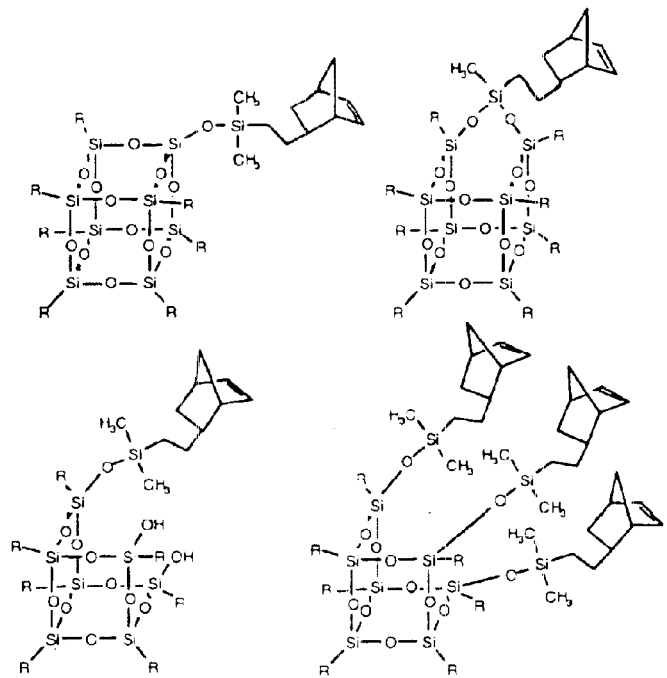
FIG. 5 shows examples of mono and tris functionalized POSS and POS nanostructure.

Structural representations of specific POSS and POS compositions that are claimed and which can be prepared using the above procedures are shown in FIG. 5. These compositions are in no way limiting and are shown to illustrate the diversity and utility of the described processes. It should further be noted that size of the POSS or POS nanostructure is not a limiting factor nor does the odd or even number of silicon or heteroatoms contained within a nanostructure limit the claimed compositions or processes.

Figure 6:
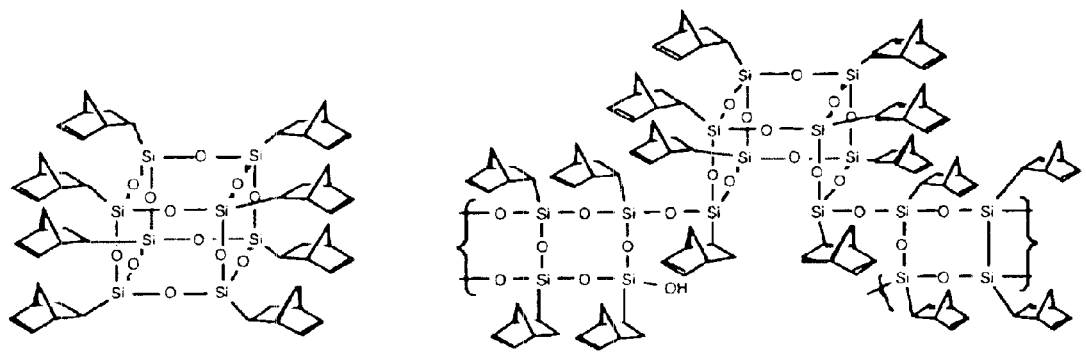
FIG. 6 shows examples of polyfunctionalized POSS, POS, and silsesquioxane resin systems.

Structural representations of specific POSS, POS, and silsesquioxane resin compositions that are claimed and which can be prepared using the above procedures are shown in FIG. 6. These compositions are in no way limiting and are shown to illustrate the diversity and utility of the described processes. It should again be noted that size of the POSS or POS nanostructure is not a limiting factor nor does the odd or even number of silicon or heteroatoms contained within a nanostructure nor the number of strained olefinic groups that can be placed on such a nanostructure limit the claimed compositions or processes.

Methods for Curing Compositions.

All of the compositions can be chemically cured using vulcanizing agents such as organoperoxides, persulfides and sulfur. Examples include AIBN (2,2'-azobisisobutyronitrile), Lupersol™ peroxides, benzoyl peroxide etc. and these are effective in 1–50 wt % loadings with loadings of 5–25 wt % being preferred. Such agents will utilize the strained olefinic carbon-carbon double bond as a polymerization point to form inter and intramolecular chemical bonds to adjacent olefinic groups.

The compositions can also be cured using a number of metal-based catalysts such as molybdenum, tungsten, and ruthenium carbenes, halides, phosphates, acetates, and salts. Examples include $WCl_6$, $MoCl_5$, (Grubb's catalyst) bis (tricyclohexylphosphine)benzylidine ruthenium (IV), (Schrock's catalyst) 2,6-disopropylphenylimido neo-phylidenemolybdenum (VI) bis(hexafluoro-t-butoxide), (Feher's catalyst, see Feher et al. *J. Am. Chem. Soc.* 1994, 116, pp 2145–2146) ([Mo(CHC($CH_3$)$_2C_6H_5$)(N(CH ($CH_3$)$_2$)$_2C_6H_4$)(c-$C_6H_{11}SiO_{1.5}$)$_7$(c-$C_6H_{11}$(($CH_3$)$_3$SiO) $SiO_{0.5}$)$_1$]$_{\geq 7}$, and cocatalysts such as organoaluminum and aluminum halides, such as methyl, ethyl propylaluminumchlorides, bromides and iodides. The catalyst-cocatalysts mixtures utilize ring opening polymerization and ring opening metathesis polymerization to form inter and intramolecular chemical bonds to adjacent olefinic groups. The elimination of ring-strain is a powerful driver of such polymerizations therefore these catalysts are effective at the 0.01 to 1000 millimole per mole of olefin level with preferably loadings of 0.1 to 20 millimole per mol of olefin.

Additionally, the compositions can be cured by reacting them with a number of di and polyfunctional silanes in the presence of a hydrosilation catalyst such as palladium, and platinum halides, olefin complexes or carbon supported versions. Silanes include but are not limited to telechelic hydride terminated oligomers such as tetramethyldisiloxane disilane, polydimethylsiloxane, and nontelechelic hydride bearing systems such as polycarbosilanes, POSS-polysilanes and polysiloxanes. Examples of effective hydrosilation catalysts include Karstedt's catalyst, Speier's catalyst, and 5% palladium supported on carbon. Such catalysts effectively promote the oxidative addition of the silicon-hydride bond of the silane to the olefinic carbon-carbon double bond of the strained-ring olefin bearing compositions claimed herein. The elimination of ring-strain during the hydrosilation process is also a driver of such polymerizations.

All of the compositions described in this disclosure can be effectively cured using the above methods. Compositions containing two or more strained olefins are particularly effective at increasing the rate of gelation and the extent of cure that can be achieve using the above mentioned procedures. The above mentioned cure techniques can be carried out using common solvents such as hexane, toluene, dichloromethane or they can be conducted with out solvents at temperatures sufficient to achieve a molten state. Through compositional formulation with mono, di, tri and polyfunctionalized combinations of the claimed strained olefin bearing compositions, the physical properties, viscocities, and cure times for neat resin mixtures can be selectively tailored to meet individual needs. Cure times ranging from seconds to hours have been achieved.

EXAMPLES

General Process Variables Applicable to All Processes

As is typical with chemical processes, there are a number of variables that can be used to control the purity, selectivity, rate and mechanism of any process. Variables influencing the process for the conversion of polysilsesquioxanes $[RSiO_{1.5}]_\infty]$ into POSS structures $[(RSiO_{1.5})_n]_{\Sigma\#}$, $[(RSiO_{1.5})_m(RSiO_{1.5})_n]_{\Sigma\#}$, $[(RSiO1.5)_m(RXSiO_{1.0})_n]_{93\ \#}$, $[(RSiO_{1.5})_m(RSiO_{1.5})_n(RXSiO1.0)_p]_{\Sigma\#}$ include but are not be limited to the following: silicon-oxygen ring size, chemical class and composition type $[RSiO_{1.5}]_\infty$ (silsesquioxane), $[(RSiO_{1.5})_n(R_2SiO)_n]_{\Sigma\#}$ (silsesquioxane-siloxane), $[(RSiO_{1.5})_m(XSiO_{1.5})_n]_{\Sigma\#}$ (silsesquioxane-silicate), effect of the organic substituents, process temperature, process solvent, process temperature, stoichiometry and the presence of a catalyst.

Listed below are a series of example processes and compositions which in no way limit the invention. Numerous related compositions and variations to the processes are easily conceived by us and others skilled in the art.

1,4-Bis(ethylnorbornenyldimethylsilyl)benzene. Chloroplatinic acid (0.023 g, 0.044 mmol) was added to a mixture of 1,4-bis(dimethylsilyl)benzene (80 g, 411 mmol) and 5-vinylnorbornene (130 mL, 910 mmol) in toluene (525 mL) at room temperature with magnetic stirring. After about 1.5 h, the solution had become yellow and very hot. A water-cooled condenser was attached and the solution cooled in liquid for 5 min. The cooling bath was removed and the solution allowed to stir at room temperature overnight. After stirring overnight, the solvent was removed in vacuo from the reaction mixture with heating to give a viscous yellow liquid (166.2 g, 93%). Product is a mixture of endo/exo isomers. Data for major isomer is given. $^1$H NMR (500 MHz, $CDCl_3$): δ 7.46 (s, 4H), 6.07 (dd, 2H), 5.84 (dd, 2H), 2.77 (s, 2H), 2.71 (s, 2H), 1.93 (m, 2H), 1.80 (m, 2H), 1.36 (m, 2H), 1.26 (s, 2H), 1.18 (d, 2H), 1.07 (overlapping multiplets, 4H), 0.73 (overlapping multiplets, 4H), 0.44 (m, 2H), 0.21 (s, 6H), 0.20 (s, 6H).

1,5-Bis(ethylnorbornenyl)-1,1,3,3,5,5-hexamethyltrisiloxane. 1,1,3,3,5,5-Hexamethyltrisiloxane (65.7 g, 315 mmol) in toluene (80 mL) was added dropwise over 1.33 h to a mixture of 5-vinylnorbornene (100 mL, 700 mmol) and Karstedt's catalyst (0.050 mL) in toluene (120 mL) at room temperature with magnetic stirring. After the addition had proceeded for about 30 min, the solution had become very hot and so was placed in an ice bath for the remainder of the addition. The addition funnel was rinsed with toluene (25 mL) and this was added to the reaction mixture. After 3 d at room temperature, the solvent was removed in vacuo from the reaction mixture with heating to give a clear, colorless liquid (134.9 g, 95%). Product is a mixture of endo/exo isomers. Data for major isomer is given. $^1$H NMR (500 MHz, $CDCl_3$): δ 6.10 (dd, 2H), 5.90 (dd, 2H), 2.80 (s, 2H), 2.74 (s, 2H), 1.94 (m, 2H), 1.83 (m, 2H), 1.40 (m, 2H), 1.31 (m, 2H), 1.22 (d, 2H), 1.09 (overlapping multiplets, 4H), 0.52 (overlapping multiplets, 4H), 0.04 (s, 12H), 0.01 (s, 6H).

1,7-Bis(ethylnorbornenyl)-1,1,3,3,5,5,7,7-octamethyltetrasiloxane. 1,1,3,3,5,5,7,7-Octamethyltetrasiloxane (75.3 g, 267 mmol) in toluene (75 mL) was added dropwise over 1.87 h to a mixture of 5-vinylnorbornene (84 mL, 588 mmol) and Karstedt's catalyst (0.050 mL) in toluene (150 mL) at room temperature with magnetic stirring. The addition funnel was rinsed with toluene (25 mL) and this was added to the reaction mixture. After 2 d at room temperature, the solvent was removed in vacuo from the reaction mixture with heating to give a clear, colorless liquid (120.6 g, 87%). Product is a mixture of endo/exo isomers. Data for major isomer is given. $^1$H NMR (500 MHz, $CDCl_3$): δ 6.10 (dd, 2H), 5.90 (dd, 2H), 2.80 (s, 2H), 2.74 (s, 2H), 1.94 (m, 2H), 1.83 (m, 2H), 1.40 (m, 2H), 1.31 (m, 2H), 1.22 (d, 2H), 1.08 (overlapping multiplets, 4H), 0.53 (overlapping multiplets, 4H), 0.05 (s, 12H), 0.04 (s, 12H).

1,3-Dicyclohexyl-1,1,3,3-tetrakis (ethylnorbornenyldimethylsilyl)disiloxane. Norbornenylethyldimethylchlorosilane (348 g, 1620 mmol) was added to 1,3-dicyclohexyltetrahydroxydisiloxane (100 g, 326 mmol) and triethylamine (250 mL) in chloroform (700 mL) at room temperature with magnetic stirring. After 4 d at room temperature, the reaction mixture was poured into water and the layers separated. The organic layer was washed with 1N HCl and water and stirred over $MgSO_4$ and activated carbon. The mixture was filtered through Celite and the solvent was removed from the filtrate in vacuo with heating to give an orange, viscous liquid. Product is a mixture of endo/exo isomers. Data for major isomer is given. $^1$H NMR (500 MHz, $CDCl_3$): δ 6.08 (dd, 4H), 5.87 (dd, 4H), 2.80 (s, 4H), 2.72 (s, 4H), 1.91 (m, 4H), 1.81 (m, 4H), 1.70 (br d, 10H), 1.37 (m, 4H), 1.25 (m, 4H), 1.20 (m, 10H), 1.06 (overlapping multiplets, 12H), 0.48 (overlapping multiplets, 10H), 0.04 (s, 24H). $^{13}$C NMR ($CDCl_3$): δ 136.79, 132.15, 49.53, 44.98, 42.55, 42.33, 32.38, 27.81, 27.09, 26.93, 25.03, 17.31, 0.25, 0.18. $^{29}$Si NMR ($CDCl_3$): δ 7.264, −69.730.

(2-Norbornenylethyldimethylsiloxy)-POSS: 2-Norbornenylethyldimethylchlorosilane (24.6 g, 0.114 mol, 1.05 eq) was added to a solution of $Cp_7T_8(OH)$ (100 g, 0.109 mol) and triethylamine (33.1 g, 45.6 mL, 3 eq) in dry tetrahydrofuran (325 mL). The reaction was carried under an inert atmosphere in a three-necked, 2 L-roundbottom flask. Immediately upon addition of the chlorosilane, a precipitate of triethylamine hydrochloride formed. After stirring for 5 h an aliquot of the reaction mixture was removed and worked up as described below and analyzed by HPLC. After 5 h the reaction is essentially complete. The reaction mixture was transferred to a separatory funnel, the reaction flask rinsed with diethyl ether and the washings added to the contents of the separatory funnel. An additional 200 mL of diethyl ether was added to the flask and the organic phase washed with successive portions of 1N HCl and saturated NaCl solution. The organic THF/Ether phase was dried over $MgSO_4$, filtered, and the concentrated by rotary evaporation. The resulting slurry was stirred with methanol and the solid collected by filtration to provide 105.9 g (89%) of Norbornenylethyldimethylsiloxy-POSS as a white powder. Because the starting 2-Norbornenylethyldimethylchlorosilane contains a mixture of exo and endo isomers, the Norbornenylethyldimethylsiloxy-POSS also contains a mixture of exo and endo isomers. Analysis by HPLC indicates product purity of greater that 99.3%. $^1$H NMR spectroscopy (major isomer 91%): 6.09 (1H dd, J=6 Hz, 3 Hz), 5.90 (1H dd, J=6 Hz, 3 Hz), 2.79 (br s, 1H), 2.73 (br s, 1H), 1.94 (m, 1H), 1.82 (m, 1H), 1.75 (m, 14H), 1.58–150 (m, 44H), 1.38 (m, 1H), 1.21 (d, 1H, J=8 Hz), 1.07 (m, 2H), 0.98 (m, 7H), 0.57 (m, 2H), 0.47 (m, 1H), 0.08 (s, 6H).

Tris(2-Norbornenylethyldimethylsiloxy)-POSS: 2-Norbornenylethyldimethylchlorosilane (73.6 g, 0.343 mol, 3.01 eq) was added to a heterogeneous solution of $Cp_7T_7(OH)_3$ (100 g, 0.114 mol) and triethylamine (57.8 g, 79.6 mL, 0.571 mol 5 eq) in dry tetrahydrofuran (300 mL). The reaction was carried under an inert atmosphere in a three-necked, 2 L-roundbottom flask. Upon complete addition of the chlorosilane, the reaction mixture was stirred for 48 h. An aliquot of the reaction mixture was removed and worked up as described below. HPLC analysis of the aliquot indicated a single product. The reaction mixture was transferred to a separatory funnel, the reaction flask washed with diethyl ether and the washings added to the contents of the separatory funnel. An additional 200 mL of diethyl ether was added to the flask and the organic phase washed with successive portions of 1N HCl and saturated NaCl. The organic phase was dried over $MgSO_4$, stirred with activated carbon, and the solvent removed by rotary evaporation. The resulting oil was stirred with MeOH, decanted and dried under vacuum at 70° C. to provide tris(2-Norbornenylethyldimethylsiloxy)-POSS as colorless viscous oil. Because the starting 2-Norbornenylethyldimethylchlorosilane contains a mixture of exo and endo isomers, the Tris(2-Norbornenylethyldimethylsiloxy)-POSS also contains a mixture of exo and endo isomers Analysis by HPLC indicates a single product. $^1$H NMR spectroscopy: 6.09 (3H dd, J=3 Hz, 6 Hz), 5.90 (3H dd, J=3 Hz, 6 Hz), 2.79 (br s, 3H), 2.73 (br s, 3H), 1.94 (m, 3H), 1.82–1.75 (overlapping multiplets, 17H), 1.58–1.38 (m, 46H), 1.21 (d, 3H), 1.06 (m, 6H), 0.86 (m, 7H), 0.62 (m, 6H), 0.47 (m, 3H), 0.08 (s, 18H).

(2-Norbornenylethyldimethylsiloxy)endodisilanol-POSS: A solution of 2-Norbornenylethyldimethylchlorosilane (24.5 g, 0.114 mol) in THF (40 mL) was added dropwise to a solution of $Cp_7T_7(OH)_3$ (100 g, 0.114 mol) and triethylamine (57.8 g, 79.6 mL, 0.571 mol 5 eq) in dry tetrahydrofuran (700 mL). The $Cp_7T_7(OH)_3$/triethylamine solution remained heterogeneous, as all of the $Cp_7T_7(OH)_3$ would not dissolve. The addition of the 2-Norbornenylethyldimethylchlorosilane was carried out over a 12 h period. Afterwards an aliquot of the reaction mixture was withdrawn and worked up (as described below). HPLC analysis of the product indicated pure (2-Norbornenylethyldimethylsiloxy)endodisilanol-POSS. The reaction mixture was transferred to a seperatory funnel and $Et_2O$ (500 mL) added. The organic phase was washed with subsequent portions of 1N HCl (2×150 μL) and saturated brine (1×100 mL). The organic phase was dried over anhydrous $MgSO_4$ and the solvent removed by rotary evaporation to provide (2-Norbornenylethyldimethylsiloxy)endodisilanol-POSS as a white solid. Analysis by HPLC indicates product purity of greater that 99%. $^1$H NMR spectroscopy (major isomer 91%): 6.09 (1H dd, J=6 Hz, 3 Hz), 5.90 (1H dd, J=6 Hz, 3 Hz), 4.18 and 4.17 (overlapping singlets, 2H), 2.79 (br s, 1H), 2.73 (br s, 1H), 1.97 (m, 1H), 1.82–1.75 (overlapping multiplets, 14H), 1.58–1.38 (m, 45H), 1.21 (d, 1H), 1.08–0.98 (overlapping multiplets, 10H), 0.62 (m, 2H), 0.47 (m, 1H), 0.120 and 0.116 (overlapping singlets, 6H).

1,3-(2-Norbornenylethyl)1,1,3,3-tetramethyldisiloxane: A solution of water (6.60 g, 0.367 mol, 1 eq) in tetrahydrofuran (60 mL) was added dropwise to a solution of 2-Norbornenylethyldimethylchlorosilane (150 g, 0.698 mol) and triethylamine (204 mL, 148 g 1.47 mol, 2.1 eq) in tetrahydrofuran (750 mL). A precipitate of triethylamine hydrochloride formed immediately upon addition of the aqueous tetrahydrofuran. The heterogeneous solution was stirred for 12 h, after which an aliquot of the reaction mixture was removed and worked up as described below. Thin layer chromatography (hexane elutant) indicated a single product. The triethylamine hydrochloride was removed by filtration, the filtrate transferred to a separatory funnel and diethyl ether (200 mL) added. The organic phase was washed with 1N HCl and saturated NaCl. The organic phase was dried over $MgSO_4$, stirred with activated carbon and filtered. The organic solvent was removed by rotary evaporation to provide 1,3-(2-Norbornenylethyl)1,1,3,3-tetramehyldisiloxane as a pale yellow oil. The final product was purified by vacuum distillation to provide 92 g (70%) of 1,3-(2-Norbornenylethyl)1,1,3,3-tetramehyldisiloxane as a colorless oil. Analysis by $^1$H NMR spectroscopy (major isomer 91%): 6.11 (1H dd, J=6 Hz, 3 Hz), 5.90 (1H dd, J=6 Hz, 3 Hz), 2.80 (br s, 1H), 2.74 (br s, 1H), 1.94 (m, 1H), 1.84 (m, 1H), 1.39 (m, 1H) 1.22 (d, 1H J=8 Hz), 1.07 (m, 2H), 0.98 (m, 7H), 0.48 (m, 3H), 0.007 (s, 6H).

Preparation of (5-norbornene-2-ethyl)Methylsiloxy Octaisobutyl-POSS: An $Et_2O$ (5 mL) solution of {(i-BuSiO1.5)$_6$(i-Bu(OH)SiO1.5)$_2$}$_{\Sigma 8}$ (890 mg, 1.00 mmol) was added a mixture of Dichloromethyl(5-norbornene-2-ethyl)silane (endo/exo=3/1, 282.3 mg, 1.20 mmol), $Et_3N$ (195 µL, 1.4 mmol), and $Et_2O$ (5 mL) at −35° C. After addition the resulting mixture was warmed to room temperature and stirred for 20 h. The mixture was hydrolyzed and extracted with diethyl ether. The organic layer was washed with brine, dried over $Na_2SO_4$. The residue was passed through a silica gel column using hexane as an eluent. Evaporation of the volatiles gave pure product (720 mg, 0.68 mmol) as a white powder in 68% yield. $^1$H NMR ($CDCl_3$) δ 0.10 (s, 9H), 0.12 (s, 3H), 0.48–0.68 (m, 72H), 0.84–1.05 (m, 194H), 1.06–1.3 (m, 18H), 1.40–1.50 (m, 4H), 1.80–1.94 (m, 32H), 1.95–2.03 (m, 3H), 2.55 (br s, 1H), 2.77 (br s, 3H), 2.78–2.83 (m, 4H), 5.93 (q, $^3$J=5 Hz, $^3$J=10 Hz, 3H), 6.04(q, $^3$J=5 Hz, $^3$J=10 Hz, 1H), 6.09–6.14 (m, 4H). $^{13}$C NMR ($CDCl_3$) δ −1.11, 15.86, 16.21, 22.58, 23.20, 23.83, 23.98, 24.06, 24.18, 25.76, 25.81, 25.89, 27.71, 29.50, 32.41, 33.10, 41.89, 41.97, 42.09, 42.65, 45.10, 45.20, 46.03, 49.61, 132.35, 136.29, 136.87, 136.96. $^{29}$Si NMR ($CDCl_3$) δ −69.25, −69.23, −69.21, −69.15, −67.04, −21.73, −21.63. Calcd for $C_{42}H_{88}O_{13}Si_9$.

Octanorbornenyl-POSS

Norbornenyltriethoxysilane (115 mmoles) reacted with tetraethylammonium hydroxide (115 mmoles) in methyl isobutyl ketone (288 mL) for 72 hours to give norbornenyl-$T_8$ cage as a white solid (10.65 g, 63.9%). $^1$H NMR (500.2 MHz, $CDCl_3$, 300K) δ 6.11 (br), 5.95 (br), 3.00 (br), 2.91 (br), 1.83 (br), 1.77 (br), 1.36 (br), 1.29 (br), 1.17 (br), 1.09 (br), 0.44 (m). $^{13}$C NMR (125.8 MHz, $CDCl_3$, 300 K) δ 21.30, 21.32, 21.43, 26.43, 26.79, 26.81, 42.28, 42.30, 42.31, 42.41, 44.23, 46.93, 50.72, 133.78, 133.97, 135.73, 137.63. $^{29}$Si NMR (99.4 MHz, $CDCl_3$, 300 K) δ −68.1, −67.8, −67.5, −67.2, −66.9, −66.7.

Octanorbornenylethyl-POSS

Norbornenylethyltriethoxysilane (115 mmoles) reacted with tetraethylammonium hydroxide (115 mmoles) in methyl isobutyl ketone (288 mL) for 72 hours to give OctanorbornenylethylPOSS cages as a white solid (10.65 g, 63.9%).

Although the present invention has been described in terms of specific embodiments, it is anticipated that alterations and modifications thereof will become apparent to those skilled in the art. It is therefore intended that the following claims be interpreted as covering all such alterations and modifications as fall within the true spirit and scope of the invention.

What is claimed is:

1. A method of making and curing a POS- or POSS-based composition, comprising the steps of:
   (a) contacting a base compostion selected from the group consisting of POSS and POS with effective amounts of a strained ring olefin in a solution in the presence of effective amounts of a catalyst which promotes addition of the ring-strained olefin to the base composition through an olefinic carbon-carbon double bond of the strained ring olefin, thereby creating a POS- or POSS-based composition with ring-strained olefinic functionality; and
   (b) curing the POS- or POSS-based composition with ring-strained olefinic functionality by reacting it with effective amounts of a mixture of (a) at least one metal-based catalyst selected from the group consisting of carbenes, halides, phosphates, acetates, and salts of molybdenum, tungsten, and ruthenium and (b) at least one cocatalyst selected from the group consisting of organoaluminum halides and aluminum halides.

2. The method of claim 1, wherein the concentration of the mixture ranges from 0.01 to 1000 millimole per mole of olefin.

3. The method of claim 1, wherein the concentration of the mixture ranges from 0.1 to 20 millimole per mole of olefin.

4. A method of making and curing a POS- or POSS-based composition, comprising the steps of:
   (a) contacting a base composition selected from the group consisting of POSS and POSS with effective amounts of a strained ring olefin in a solution in the presence of effective amounts of a catalyst which promotes addition of the ring-strained olefin to the base composition through an olefinic carbon-carbon double bond of the strained ring olefin, thereby creating a POS- or POSS-based composition with ring-strained olefinic functionality; and
   (b) curing the POS- or POSS-based composition with ring-strained olefinic functionality by reacting it with effective amounts of at least one difunctional or polyfunctional silane in the presence of effective amounts of a catalyst selected from the group consisting of palladium halides, platinum halides, palladium-olefin complexes, platinum-olefin complexes, carbon-supported palladium halides, carbon-supported platinum halides, carbon-supported palladium-olefin complexes, and carbon-supported platinum-olefin complexes.

5. A method of making and curing a POS- or POSS-based composition, comprising the steps of:
   (a) contacting a base composition selected from the group consisting of POSS and POS with effective amounts of a strained ring olefin in a solution in the presence of effective amounts of a catalyst which promotes addition of the ring-strained olefin to the base composition through an olefinic carbon-carbon double bond of the strained ring olefin, thereby creating a POS- or POSS-based composition with ring-strained olefinic functionality; and
   (b) curing the POS- or POSS-based composition with ring-strained olefinic functionality by reacting it with effective amounts of a vulcanizing agent selected from the group consisting of organoperoxides, persulfides, and sulfur.

6. The method of claim 5, wherein the concentration of the vulcanizing agent ranges from 1 to 50 weight %.

7. The method of claim 5, wherein the concentration of the vulcanizing agent ranges from 2 to 25 weight %.

* * * * *